(12) United States Patent
Scott

(10) Patent No.: US 6,402,763 B1
(45) Date of Patent: Jun. 11, 2002

(54) METHOD AND APPARATUS FOR EXTRICATING INGROWN HAIRS AND RELIEVING PAIN AND DISCOMFORT ASSOCIATED WITH PSUEDOFOLICULLITIS BARBAE (PFB)

(76) Inventor: Ronald W. Scott, 7301 Park Heights Ave. Apt. 207, Baltimore, MD (US) 21208

( * ) Notice: Subject to any disclaimer, the term of this patent is extended or adjusted under 35 U.S.C. 154(b) by 0 days.

(21) Appl. No.: 09/726,095

(22) Filed: Nov. 29, 2000

(51) Int. Cl.[7] .............................................. A61B 18/04
(52) U.S. Cl. ........................................ 606/133; 30/155
(58) Field of Search ................... 606/167, 131–133; 30/155; 132/76.2, 90

(56) References Cited

U.S. PATENT DOCUMENTS

| 368,198 | A | * | 8/1887 | Eaton |
| 1,089,019 | A | | 3/1914 | Swasey |
| 1,113,168 | A | * | 10/1914 | Henkel |
| 1,268,558 | A | * | 6/1918 | Faix |
| 2,224,384 | A | | 12/1940 | Gratiot |
| 4,098,157 | A | | 7/1978 | Doyle ........................ 83/128 |
| 4,709,481 | A | | 12/1987 | Moore ......................... 30/356 |
| 4,790,316 | A | | 12/1988 | Bogdan |
| 4,994,061 | A | | 2/1991 | McPherson .................. 606/43 |

* cited by examiner

Primary Examiner—Michael J. Milano
Assistant Examiner—William W. Lewis

(57) ABSTRACT

A device for extricating ingrown hairs comprising a housing and a blade member disposed in the housing. The blade member has a proximal portion and a distal portion with the distal portion terminating in a hook member and the proximal portion attached to the housing via an attachment means. The attachment means provides the hook member with an adjustable tension for rotatable hair removal.

9 Claims, 3 Drawing Sheets

METHOD AND APPARATUS FOR EXTRICATING INGROWN HAIRS AND RELIEVING PAIN AND DISCOMFORT ASSOCIATED WITH PSUEDOFOLICULLITIS BARBAE (PFB)

FIELD OF THE INVENTION

The present invention relates generally to a method and apparatus for removing objects from the skin. More particularly, the present invention relates to a method and apparatus for removing objects from the skin and remedying the effects of pseudofolicullitis barbae (PFB) or ingrown hairs.

BACKGROUND OF THE INVENTION

Pseudofollicultis Barbae (PFB) is a painful, chronic, distressing and potentially disfiguring dermatological disorder that occurs predominantly in people of color. As illustrated in FIG. 4A, PFB, a cutaneous affliction caused by shaving arises as a result of a curved hair 100 that emerges through the dermal layer of the skin 110 from a curved follicle 120 at an acute angle and continues to curve in its external growth path. Continued growth and curvature leads to the hair tip penetrating the skin 130 forming a false follicle a few millimeters away from the point of emergence. Such intrusion of the tip penetrating the skin is often times characterized by erythematous papules, pustules and occasional hypertrophic keloidal scar formation in a typical inflammatory reaction of skin penetration by a foreign object.

In the past, to remedy PFB, ordinary household tweezers were often employed. While tweezers could be used to remove an ingrown hair when a portion of the ingrown hair was exposed, tweezers were generally ineffective in those instances where the ingrown hair grew entirely under the skin. Even in those instances where a portion of the ingrown hair was exposed, it was often hard to grasp. Furthermore, often while using tweezers to extricate an ingrown hair, the entire hair was pulled out of its follicle, leaving the empty follicle subject to a potential Staphylococcus infection. For the well being of the PFB sufferers, it is not advisable to remove the entire hair. It is medically preferable to simply extricate the non-rooted end of the ingrown hair, so that it can be shaved along with the surrounding hairs.

In the past it has also been common to use a needle or a straight pin in attempting to extricate an ingrown hair from the skin. Such needles and pins, however, provide no means by which to catch the hair and pull it to the surface. The use of a needle or pin was additionally unsatisfactory since it often caused painful wounds to the PFB sufferer as the pustule or papule was probed or lanced by the sharp end of the needle or pin. The use of needles and pins is further unsatisfactory because these devices can be easily inserted under the skin to a painful depth because of their extremely sharp points and narrow cross section. Finally, such needles and pins are often not kept in a sanitary condition. As a result, the person desiring to extricate an ingrown hair uses an unsanitized pin or needle found in a sewing kit, household drawer, or other catchall compartments.

Another problem associated with the above mentioned ingrown hair removal techniques is that the devices used to remove the ingrown hair are always rigid devices. Thus, there is no flexibility in adjusting the amount of force exerted. For example, a user may be "heavy-handed" and exert too much pressure in trying to remove an ingrown hair while on the other hand, a user may be "light-handed" and not apply enough pressure to remove the hair and thus irritate the skin even more.

Thus, there remains a need for an improved method and apparatus capable of dislodging ingrown hairs with a rotatable hook/blade for an adjustable hair removal process that minimizes trauma to the PFB site.

SUMMARY OF THE INVENTION

A device for extricating ingrown hairs comprising a housing and a blade member disposed in the housing. The blade member has a proximal portion and a distal portion with the distal portion terminating in a hook member and the proximal portion attached to the housing via an attachment means. The attachment means provides the hook member with an adjustable tension for rotatable hair removal.

These and various other characteristics and advantages of the present invention will become readily apparent to those skilled in the art upon reading the following detailed description and claims, and by referring to the accompanying drawings.

DESCRIPTION OF THE PREFERRED EMBODIMENT

Figure 1:
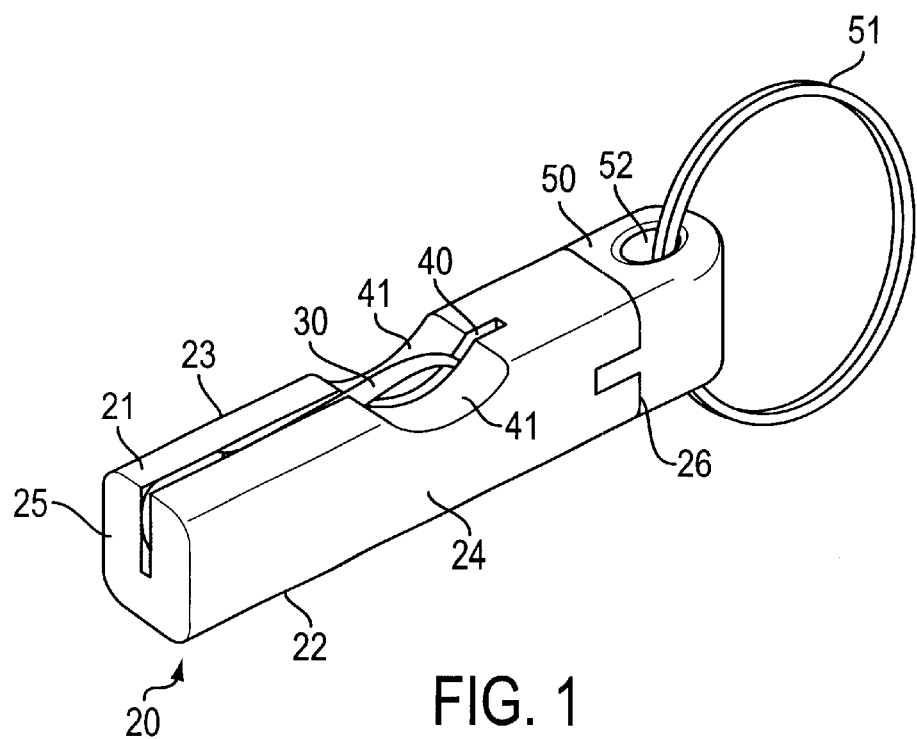
FIG. 1 depicts a perspective view of an instrument in a carrying position constructed according to an embodiment of the present invention.
Figure 3:
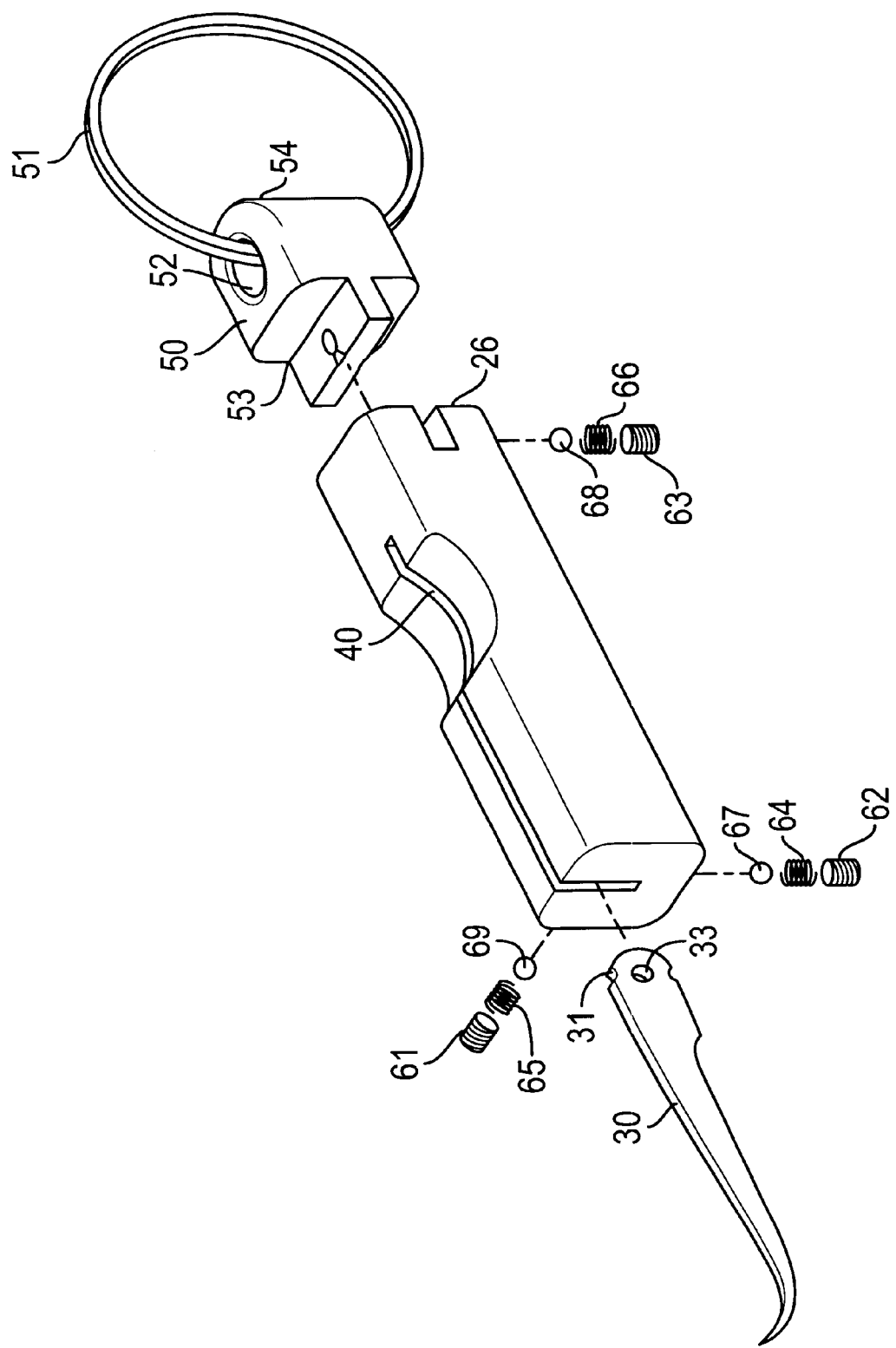
FIG. 3 depicts a perspective view of the instrument in FIG. 2 in a disassembled position according to an embodiment of the present invention.

FIG. 1 depicts a perspective view of an instrument 1 in a carrying position constructed according to an embodiment of the present invention. Referring now to FIG. 1, the instrument 1 is useful for relieving the pain and discomfort associated with pseudofolicullitis barbae (PFB) by rotatably extricating the non-rooted end of the hair from the layers of skin in which it has penetrated. More particularly, the instrument 1 includes an elongated housing member 20, generally square or rectangular in cross section, formed by upper surface 21, lower surface 22, side surface 23 and 24, and front and back surfaces 25 and 26, respectively. Back surface 26 is best shown in FIG. 3 and will be described in further detail.

According to one embodiment of the present invention, housing member 20 may be generally octagonal in shape for better handling. The fact that the instrument 1 is octagonal allows it to be maneuvered very easily in the user's hand. Housing member 20 also includes the thumb depression member 41. The thumb depression member 41 offers two advantages.

The first advantage allows a hook member, described in greater detail later in this specification, to be extracted with one thumb and index finger. The second advantage offered by the thumb depression member 41 is that it acts a placement point for the fingers when extricating ingrown hairs. Housing member 20 can be made of aluminum treated with sulfuric anodized or other similar material such as passibated stainless steel. Thus, housing member 20 will not oxidize, is non-conductive and colors of black, blue, gold, maroon, green and clear are used as identifiers.

Figure 2:
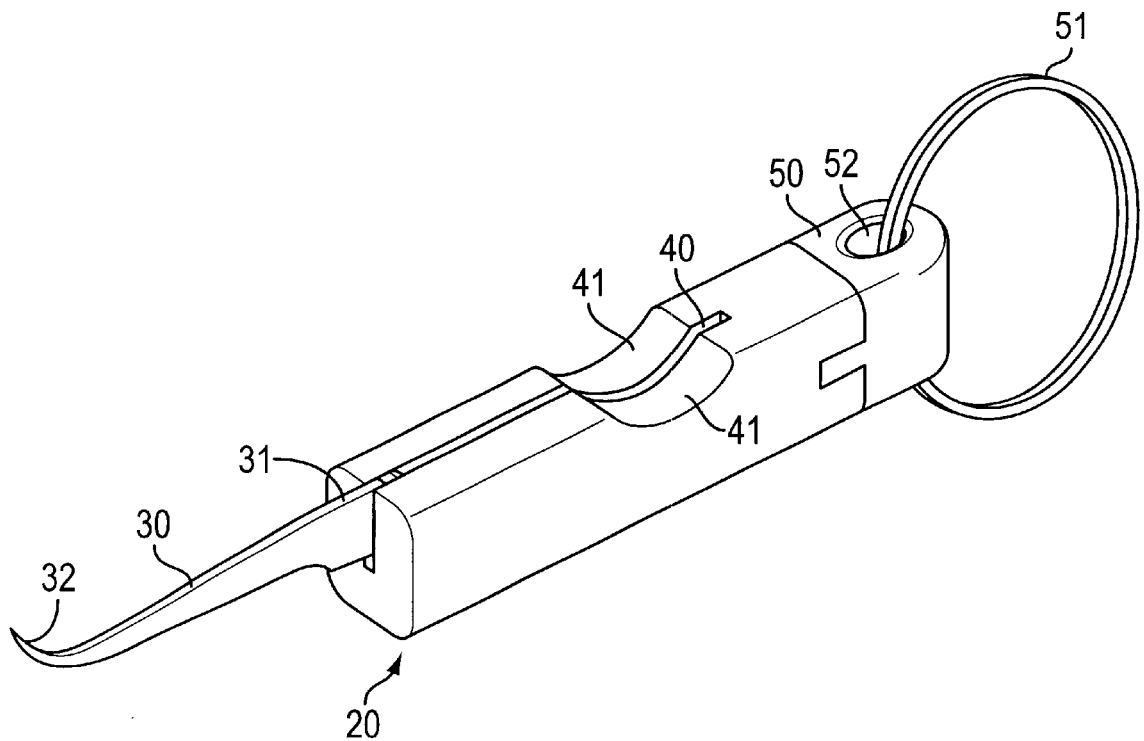
FIG. 2 depicts a perspective view of the instruments in FIG. 1 in an operable position according to an embodiment of the present invention.

Instrument 1 further includes a blade member 30 as shown in greater detail in FIG. 2, which includes a proximal portion, 31 and a distal portion 32. The proximal portion 31 is attached to the housing member 20 and is located substantially in a center portion of the front surface 25 of the housing member 20. The distal portion 32 terminates in a hook member. The blade member 30 is preferable made of stainless steel or another metal with similar qualities. The construction material of blade member 30 is strong, easy to clean and maintain, and immune to rusting and ordinary corrosion. Blade member 30 can be sanitized and autoclaved. Blade member 30 can pierce the skin when necessary to extricate an unexposed ingrown hair. In the alternative, instrument 1 could be injection molded of sanitary, non-toxic, hypoallergenic inexpensive plastic or flexible plastic. However, within the scope of this invention, the blade may vary in design and in construction material.

According to one embodiment of the present invention, blade member 30 is disposable and easily replaced as shown in FIG. 3. The hook member formed on distal portion 32 is sharp enough to pierce the skin dermis or epidermis and dislodge the hair without causing damage to the PFB site, which normally results in scars, hyperpigmentation, black spots or even keloids. The size of the blade member 30 is approximately 1.75 inches, which is approximately 43% of the entire length of instrument 1. In a preferred embodiment of the present invention, the overall length of the blade member 30 was 39% in comparison to the length of the entire instrument including a ring portion, described in greater detail later.

Instrument 1 further includes an aperture 40 disposed in the upper surface 21 of housing member 20 for the accommodation of said blade member 30 when the instrument 1 is in a carrying mode as will be further described. Aperture 40 is generally elongated and is designed to protect blade member 30 when not in use. Aperture 40 is also designed such that the retractable blade member 30 protects the user from being inadvertently stuck. Instrument 1 further comprises an end cap portion 50 including a ring member 51. Referring to FIG. 3 end cap portion 50 has a proximal portion 53 and a distal portion 54, wherein the proximal portion 53 is capable of being detachably mounted to said proximal portion 26 of housing member 20 and distal portion 54 includes an aperture 52 defined therein for accommodating ring member 51. End cap portion 50 is used for detachably connecting to housing member 20 so that instrument 1 can be portable. Ring member 51 is used to connect instrument 1 to a key chain or other device, which will make it portable and easy to carry.

Figure 4A:
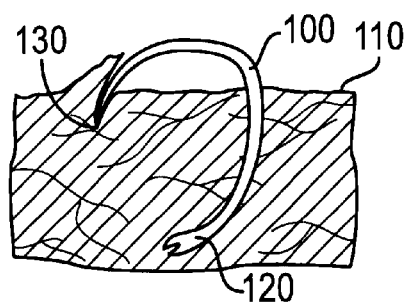
FIG. 4A depicts a cross sectional view of an area of skin having one form of PFB.

Referring to FIG. 3, instrument 1 farther includes an attachment means defined by stainless steel set screw members 61, 62 and 63 as well as, stainless steel spring member 64, 65, 66 and stainless steel bearings 67,68 and 69. Steel spring member 64, 65, 66 can act as a biasing means to adjust the tension in the blade. Proximal portion 31 of blade member 30 includes an aperture 33 provided to accept bearing member 69 which keeps tension on the blade. Blade member 30 is further supported by set screw 62, which is used to adjust the tension on blade member 30. For example, turning set screw 62 in either a clockwise or in a counterclockwise direction increases or decreases the amount of tension applied to spring member 64 and bearing 67 which increases or decreases the amount of tension in blade member 30. To extricate an ingrown hair that has grown in a loop configuration as shown in FIG. 4A, a light application of blade member 30 may be all that is needed. Thus, the user can adjust set screw 62 by turning it in the counterclockwise direction (i.e., loosening screw 62) which reduces the amount of tension on the spring, bearing and blade member 30. On the other hand, the user may desire to apply more pressure in order to extricate an ingrown hair. Thus, the user can adjust sets crew 62 by turning in the clockwise direction (i.e., tightening screw 62) which increases the amount of tension on the spring, bearing and blade member 30. Thus, the user can remove and replace the blade member 30 by adjusting set screw 61, clockwise or counterclockwise.

Figure 4B:
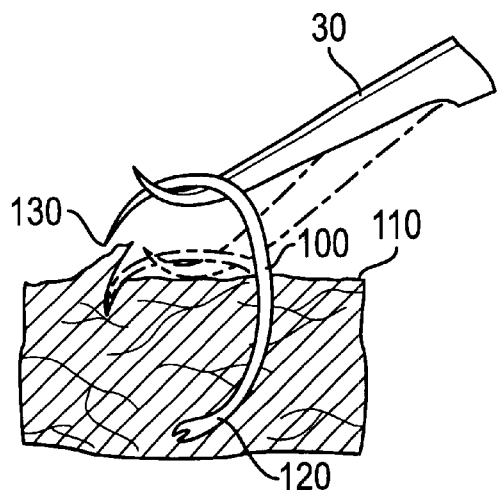
FIG. 4B depicts a cross sectional view of the instrument in FIG. 2 in an operational position rotatably extricating an ingrown hair tip from a PFB site.
Figure 5:
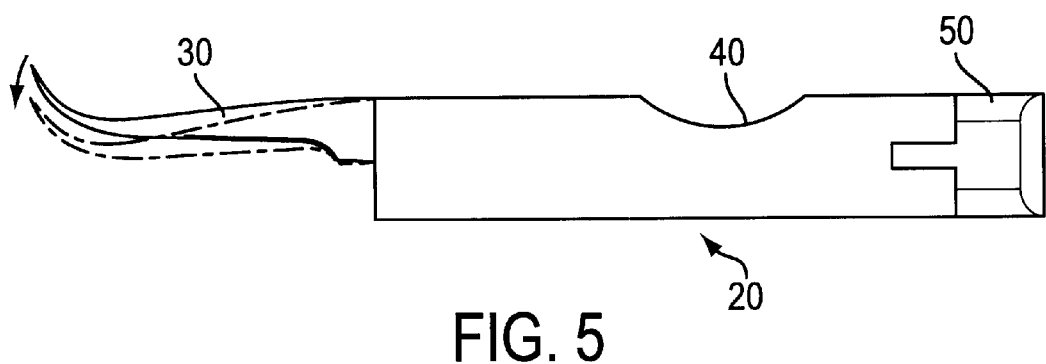
FIG. 5 depicts a side elevation of the instrument in a rotatable motion according to an embodiment of the present invention.

FIG. 4B depicts a cross sectional view of an area of skin having one type of ingrown hair being extricated by a method utilizing the instrument 1, according to one embodiment of the present invention. A method for extricating ingrown hairs from the skin includes grasping a device having a housing and a blade member disposed in the housing, with the blade member having a proximal portion and a distal portion and the distal portion terminating in a hook and the proximal portion attached to the housing by a set screw. The blade member being made of a stainless steel. The method also includes the steps of inserting the hook under an ingrown hair and using the tension in the blade to extricate the hair. The tension of the blade allows for tip rotation without additional finger pressure on the PFB site and eliminates any sharp fulcrum, which would be painful during ingrown hair extrication. Thus, this method of extricating ingrown hairs is an improvement in safety and efficiency over the devices previously known or mentioned. There is disclosed herein an instrument for use in efficiently and sanitarily extricating an ingrown hair from the skin. The instrument includes a housing and a blade member disposed in the housing. The blade member has a proximal portion and a distal portion; the distal portion terminating in a hook and the proximal portion attached to the housing by an attachment means. The attachment means provides the hook member with an adjustable tension for rotatable hair removal. The instrument allows for a one-handed procedure. Thus, it is possible to hold the instrument in one hand and use the other hand to manipulate the face, hold a mirror or any other equipment needed in the extricating process.

What is claimed is:

1. A method for extricating ingrown hairs from the skin comprising:

grasping a device having a housing and a blade member disposed in the housing, the blade member having a proximal portion a distal portion a top portion and a bottom portion, the distal portion, terminating in a hook member that curves toward the top portion, and the proximal portion attached to said housing via an attachment means with the attachment means providing the hook member with an adjustable tension means located to contact the bottom portion of the blade for rotatable hair removal;

inserting said hook under an ingrown hair; and lifting the ingrown hair from the skin.

2. The method according to claim 1, wherein the housing includes an aperture therein, the aperture accommodating said blade member when said device is in a carrying position.

3. The method according to claim 1 wherein said blade member is made out of a stainless steel.

4. The method according to claim 1, wherein said blade member is made out of a plastic.

5. The method according to claim 1, wherein said attachment means is a biasing means used to adjust the tension on the blade member.

6. The method according to claim 1, further comprising a cap portion, detachably mounted to the housing.

7. The method according to claim 2, wherein said aperture is generally elongated.

8. The method according to claim 1, further comprising the step of inserting said hook member to engage at least one loop of an ingrown hair.

9. A device for extricating ingrown hairs comprising:

a housing; and a blade member disposed in the housing, the blade member being made of stainless steel and having a proximal portion, a distal portion, a top portion and a bottom portion, the distal portion terminating in a hook member that curves toward the top portion, and the proximal portion attached to said housing via a biasing means located to contact the bottom portion of the blade;

wherein said biasing means provides the hook member with an adjustable tension for rotatable hair removal.

\* \* \* \* \*